United States Patent [19]
Albert

[11] Patent Number: 5,184,718
[45] Date of Patent: Feb. 9, 1993

[54] DISPOSABLE DENTURE CONTAINER

[76] Inventor: Harvey Albert, 34 Pond Dr., Walpole, Mass. 02081

[21] Appl. No.: 780,026

[22] Filed: Oct. 21, 1991

[51] Int. Cl.⁵ .............................................. A61B 19/02
[52] U.S. Cl. .................................... 206/63.5; 134/93; 206/83; 206/205
[58] Field of Search ........................ 206/83, 63.5, 205; 132/308, 309, 324, 326; 68/213; 134/93, 182, 199

[56] References Cited

U.S. PATENT DOCUMENTS

| | | | |
|---|---|---|---|
| 2,102,643 | 12/1937 | Pellegrini | 206/83 X |
| 2,163,862 | 6/1939 | Wing | 206/83 X |
| 2,196,566 | 4/1940 | Sabattis | 206/83 |
| 2,541,595 | 2/1951 | Marshall et al. | 206/83 X |
| 2,565,899 | 8/1951 | Wilcox | 206/83 X |
| 2,620,919 | 12/1952 | Passmore | 206/83 |
| 2,973,767 | 3/1961 | Cohen | 206/83 X |
| 3,105,376 | 10/1963 | Haslett | 68/213 |
| 3,732,973 | 5/1973 | Crawford | 206/83 X |
| 4,666,037 | 5/1987 | Weissman | 206/63.5 |
| 4,697,700 | 10/1987 | Weissman | 206/83 |
| 4,724,855 | 2/1988 | Jackson et al. | 134/93 |
| 4,991,759 | 2/1991 | Scharf | 206/63.5 X |

Primary Examiner—Bryon P. Gehman
Attorney, Agent, or Firm—Alvin Isaacs

[57] ABSTRACT

A disposable container adapted for a single daily use for storing and cleaning dentures when not worn is disclosed. The container, which is particularly suitable for use in hospitals and nursing institutions as well as at home, is characterized as being disposable after a single use, of simple, convenient but elegant construction, inexpensive and sanitary, and carrying its own individual supply of cleanser.

8 Claims, 2 Drawing Sheets

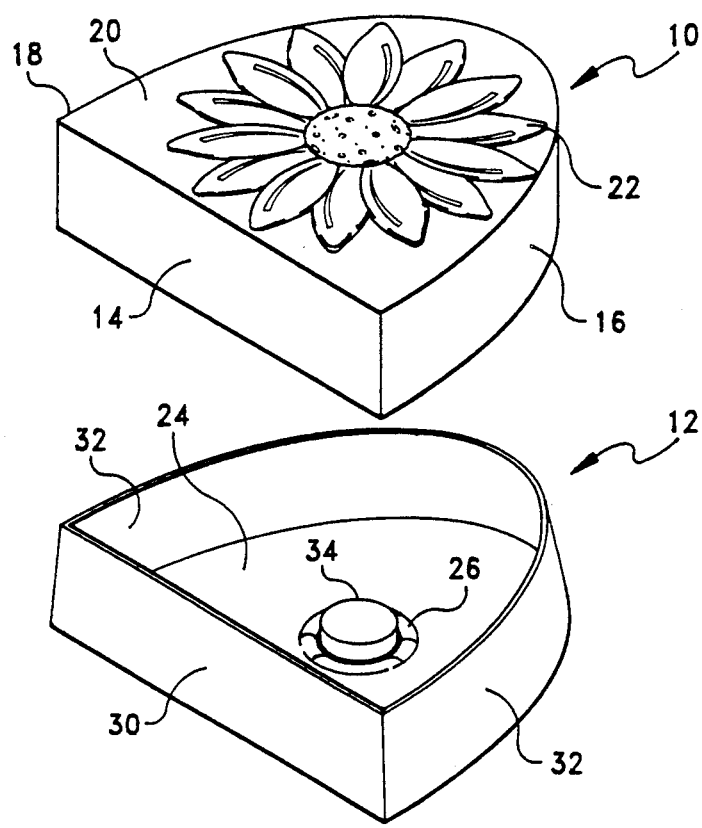
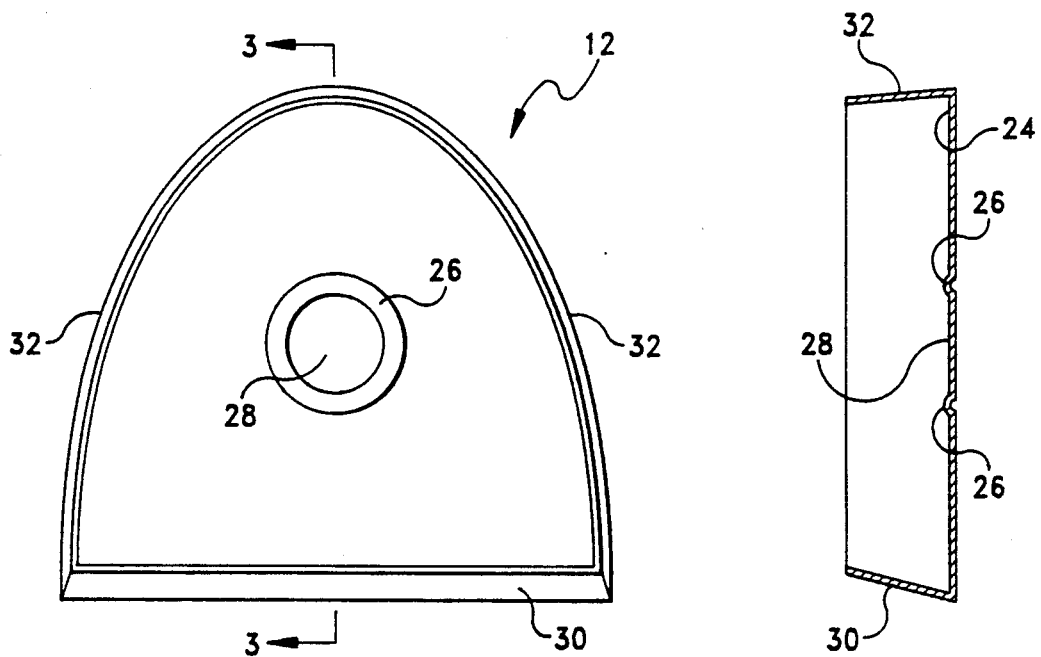
FIG. 1
FIG. 2
FIG. 3

DISPOSABLE DENTURE CONTAINER

BACKGROUND OF THE INVENTION

Denture containers for storing dentures when not in use, e.g. at night, are generally well known. While not intended to be a comprehensive survey of the art, the following patents may nevertheless be taken as representative.

U.S. Pat. No. 2,122,583 issued to Parizot discloses a holder in the shape of a bottom plate adapted to clamp about a denture to hold it firmly in place when inserted in a closed container having a liquid dentifrice, so that the container can be shook for cleaning action without damaging the denture.

U.S. Pat. No. 2,163,862 of Wing relates to a holder for dentures or other articles wherein a perforated receptacle appends from the container lid. The denture can be placed in the receptacle and then immersed in a cleaning liquid, thereby satisfying the stated objective of permitting cleaning while "avoiding to a considerable extent soiling of the fingers."

In U.S. Pat. No. 2,375,645 issued to Gordon, a dental plate container is disclosed which provides "protective safety and sanitary protection." In Col. 1, the need is discussed for a portable container of this description, noting that may wearers have to keep their plates at night in water in an open glass or container. As best seen in FIG. 2, the patented container is designed to hold both upper and lower plates.

U.S. Pat. No. 2,444,294 issued to Jones teaches a dental plate container having an adjustable holder for securely engaging the dental plate. In Col. 2 it is mentioned that the inside of the container lid may be provided with an absorbent pad which can be saturated with a germicidal fluid.

U.S. Pat. No. 2,541,595 of Marshall et al discloses a denture container which is leak-proof for safely and inconspicuously storing dentures. The container has a basket-like perforated inset in which the denture is placed. The container is filled with water or a dental solution and the inset then placed in the container.

U.S. Pat. No. 2,565,899 issued to Wilcox teaches a portable cleaning device for artificial dentures, in which the denture may be firmly held within an enclosure containing a cleaning solution while manually imparting vigorous agitating movement to the container and solution. A threaded adjustable dental support is disposed within the container. In use, the support is adjusted to the proper elevation for the denture. Cleaning is effected by adding cleaning fluid and shaking.

U.S. Pat. No. 2,620,919 of Passmore relates to portable containers for dentures and the like which are said to be characterized by their simplicity, durability, low cost and convenience. The container is designed to protect against breakage if dropped and from contamination from both internal and external bacteria. It consists of two sections which together form a ball having cushioning bodies on the inside. Since the container is clearly not adapted for cleaning, Applicant does not understand the statement about protection from "internal bacteria".

U.S. Pat. No. 2,973,767 of Cohen describes a denture container which retains water and acts as a container for a toothbrush also. It comprises an arrangement of elements including, in order, a main container, an auxiliary container, a cover, a denture holder and another cover. The container will store dentures of different sizes along with a cleaning fluid.

U.S. Pat. No. 3,732,973 issued to Crawford relates to a combined denture case and brush. After cleaning, the denture can be soaked in a cleaning receptacle of the container and the brush cleaned and reinserted in a brush receptacle of the container until the next cleaning.

Finally, U.S. Pat. No. 4,724,855 of Jackson relates to a denture power washer having a denture cleaner storage compartment housing a dry cleaner. The power washer has a washer container, a lid within which the denture cleaner storage compartment is situated, and a drain at the bottom of the container. For purposes of illustration, the dry cleanser in the storage compartment is shown to be a tablet. In use, the lid is removed and a denture placed in the container. The washer is then placed under a faucet to initially rinse off the denture. The cover is then removed from the cleanser storage compartment and the chemical cleanser is deposited within the container. The lid and cover are then reapplied and the washer inverted and filled to a given level with water through the drain at the bottom. It is left inverted for soaking. The lid is then removed and the denture rinsed under flowing water to complete the washing cycle.

Despite the state of the art with respect to denture containers, as illustrated by the above-mentioned patents, there is still a great need for an inexpensive container for storing and cleaning dentures and which can be discarded after a single use.

The task of this invention, stated simply, is to provide a denture container of the foregoing description.

BRIEF DESCRIPTION OF THE INVENTION

In accordance with this invention the task is solved by providing a throw-away container consisting of a bottom member and a cover member of the general configuration of a denture and which are adapted to receive for storage therebetween a full set of dentures, the bottom member having means for receiving a dentifrice, and a dentifrice in solid form for cleaning the denture when water is added being disposed in the dentifrice receiving means of the bottom member.

BRIEF DESCRIPTION OF THE DRAWINGS

FIG. 1 is an exploded view showing the top and bottom members of the preferred denture container of this invention;

FIG. 2 is an elevation view of the bottom member shown in FIG. 1;

FIG. 3 is a sectional view taken along lines 3,3 of FIG. 2;

DETAILED DESCRIPTION OF THE INVENTION

Figure 4:
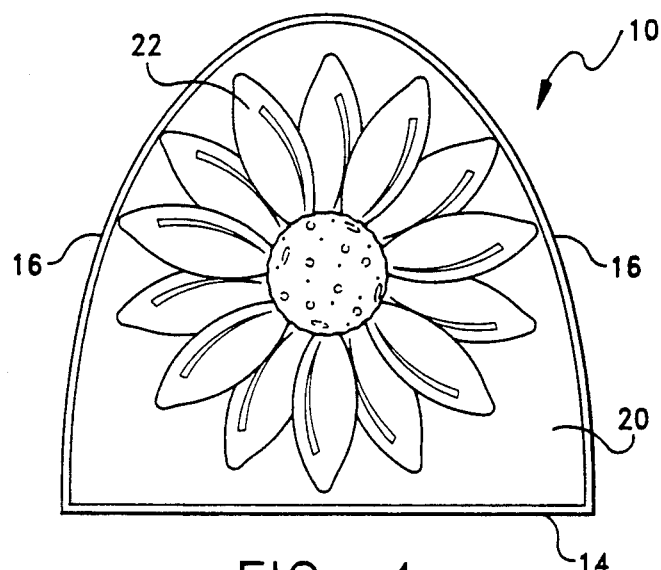
FIG. 4 is an elevation view of the top member shown in FIG. 1.
Figure 5:
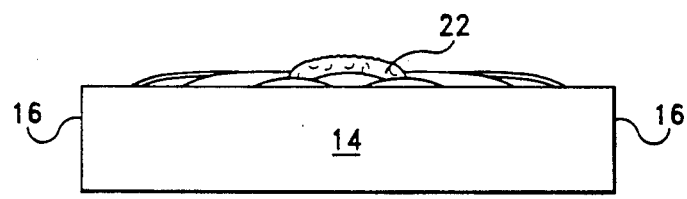
FIG. 5 is a front view of the top member.

Healthy people living at home who wear dentures generally take them out at night before they go to sleep. Typically, the dentures are placed in a glass or other receptacle at bedside or in the bathroom, assuming they are not simply placed on a shelf or other article in the bathroom. As will be readily understood, such placement of the denture when not worn is not sanitary. The denture should not be placed in the mouth again without cleaning with a cleanser including a bactericide such as those commercially available. e.g. "EFFERDENT" (trademark of Warner-Lambert) and "POLIDENT" (trademark of Block Drug). Additionally, if placed in a glass or the like container which is not cleaned after each use, the glass becomes a breeding ground for bacteria as well as possessing an unplesant odor. Moreover, the unpleasant task is presented for cleaning the receptacle which usually is both filmy and grimy.

These problems are of a magnitude greater when one considers the sick and the aged in nursing homes and medical care institutions. Unable to attend to their own personal needs, the dentures will generally sit at bedside, on a table or in a glass, unless the person is attended to daily by family or by a staff member able to attend to their personal needs. Moreover, staff members or others attending to the personal needs of the incapacitated sick and aged are extremely reluctant to clean their receptacles for dentures, let alone those of others. This is particularly true in the light of the current well-known health problems It is to these concerns that the present invention is directed.

The nature and objects of the invention may best be understood by reference to the accompanying illustrative drawings taken in conjunction with the following detailed description.

As shown in FIGS. 1-5, the denture container has separate top and bottom members 10 and 12, respectively, in the shape of a denture.

Top member 12, adapted to fit over the bottom member 10 to confine the denture(s) therebetween, has a straight vertical wall 14 element, a curved vertical wall element 16 and a cover or lid 18. The curved vertical wall element 16 extends from one side edge of the vertical wall element 14 to the other. Wall elements 14 and 16, which define the shape of the top member are joined to each other and to the periphery of cover 18. While cover 18 may, if desired, be substantially planar in configuration, for esthetic reasons only it is shown to comprise a planar surface 20 and an embossed floral design portion 22 which is illustrated to be in the form of a daisy.

Bottom member 14 is of substantially the same shape as top member 12, but is of slightly smaller dimensions to permit the top member 12 to slide over at least a portion of the depth of the bottom member. Bottom member 14 has a base element 24 on which the denture is adapted to be seated. Like the top member 12, it has a straight vertical wall element 30 and a curved vertical wall element 32 extending from one side edge of the straight vertical wall element 30 to the other. The wall elements 30 and 32 are joined to each other and to the base element 24. For ease of mounting the top member over the bottom member, the upstanding or straight vertical wall element 30 of the bottom member 14 is preferably slanted inwardly, as seen in FIG. 3.

Figure 6:
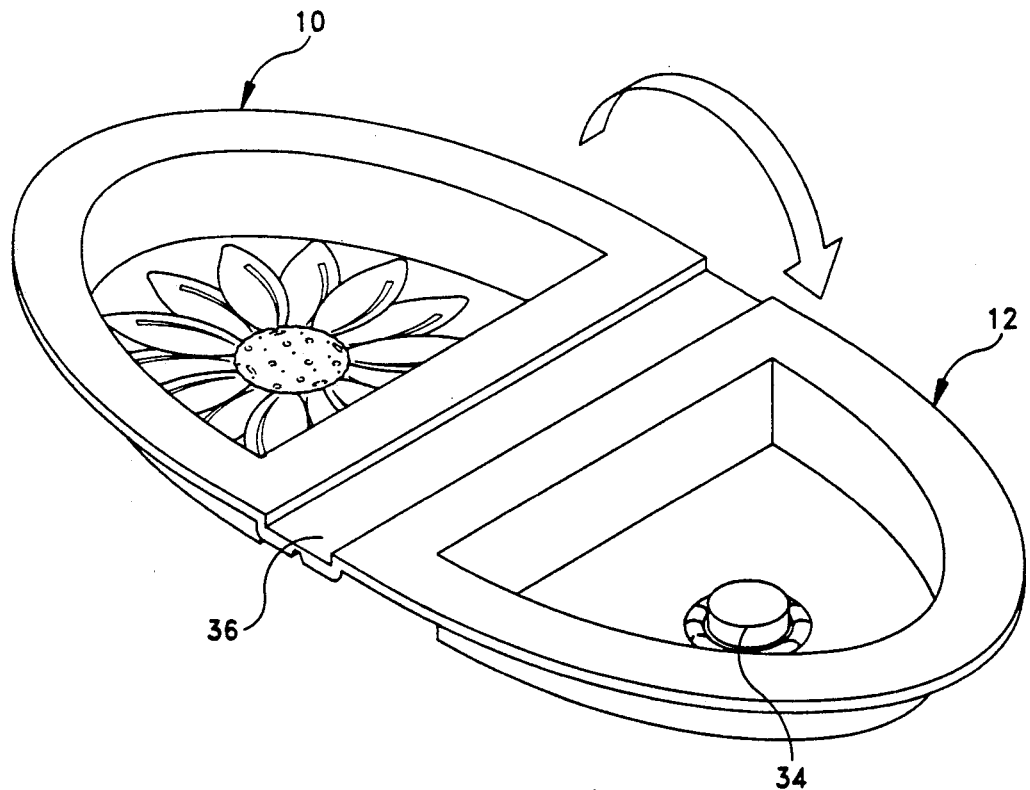
FIG. 6 is a perspective view of an alternate embodiment of the invention.

The base element 14 is provided with an annular upstanding rim element 26 defining a space 28 (herein characterized as a "well") for receiving a solid water-soluble dentifrice for cleaning the denture. The dentifrice is preferably in the form of a table 34, as shown in FIGS. 1 and 6. However, it will be appreciated that it can also be in the form of small discrete particles. In any case, space 28 should preferably be substantially centrally disposed on base element 24. In the preferred form, rim 26 should be at least as thick as the tablet confined therebetween. Accordingly, it follows that the tablet should be as thin as possible.

Since the novel denture container of this invention is intended to be discarded after a single use, the top and bottom members forming the denture container will preferably be made of a suitable inexpensive plastic material such as polyvinyl chloride, a polyolefin such as polyethylene, styrene, etc. It may be transparent or opaque, e.g. colored, according to individual choice. While some users prefer the transparent form so that the dentures are visible within the container, others find the sight of the dentures to be objectionable. Materials of the foregoing description suitable for making the container will be readily apparent in the light of this description and their selection may be a matter of individual choice. Accordingly, the materials to be used per se comprise no part of this invention.

In like manner, the method of manufacture per se comprises no part of this invention. They may, for example, be made by known injection molding techniques.

While the denture containers and dentifrices to be incorporated therein may if desired be separately packaged, in the preferred embodiment contemplated by this invention, they will be packaged for sale with a dentifrice in each denture container. In this manner, the users will have at their disposal for convenience of use one or a plurality of the containers, each with its individual dentifrice supply and ready for use cleaning and storing the dentures.

FIG. 6 shows another embodiment of the invention wherein like elements are numbered the same. The embodiment of FIG. 6 differs essentially from the one described above and shown in FIGS. 1-5 only that the top and bottom members are hinged together at 38 to provide a unitary element rather than one where the respective elements are separable. Preferably hinge 38 as shown in FIG. 6 is a living hinge provided by molding the container as a single element from a flexible polymeric material. So-called living hinges are of course well known and may for example be slightly thinner than the rest of the container to maximize flexibility for moving the members from an open position for inserting the denture to a closed position for storage.

The bottom member 12 in either embodiment should be of the general shape of the denture and will of course possess sufficient dimensions to accommodate the denture. The depth of the bottom member should be such that when water is added to solubilize the dentifrice, the denture contained therein will be submerged for cleaning.

By way of illustration. The straight vertical wall element 30 may be on the order of 3.25 to 3.50 inches from one side edge to the other; the distance from the straight wall element to the center or tip of the curved vertical wall member 32 (as measured from the center of element 30 in a line perpendicular to element 30 and extending to element 32) may be on the order of 3.00 to 3.25 inches; and the vertical walls may extend on the order of 1.75 to 2.00 inches from the base 24 on which the denture is to be seated. The rim 26 may be on the order of one-eight to three sixteenth of an inch high and provide a well or space 28 therebetween on the order of five-eighths to one inch in diameter.

In use, the denture may first be rinsed after removal from the mouth and then placed within element 12. (If a dentifrice is not initially provided within the container, it will be appreciated that it should be seated within space 28 before inserting the dentifrice.) Water is then added at a level to submerge the denture and the top member 10 positioned over the bottom member to close the container.

From the foregoing discussion it will thus be seen that the present invention provides an elegant means for storing and cleaning dentures. According to the invention, an inexpensive throw-away container having its own one-time supply of dentifrice is provided. While it finds great utility in the home, it is particularly useful in nursing homes, hospitals and other institutions for the sick and the aged who at best are capable of only minimal personal care.

It will be appreciated that the denture containers of this invention are capable of various modifications without departing from the scope of the invention herein contemplated.

For example, in lieu of providing a single well containing dentifrice, as described above and shown in the drawings, a plurality of such wells may be disposed in spaced relationship along base 24. Additionally, while these wells have been described has being essentially in the same plane as base 24, they may instead be recessed or an intaglio provided by stamping base 24. As heretofore alluded to, the wells may contain dentifrice in pellet, powder, or other solid form rather than as tablets. While the rim defining the well for receiving the dentifrice is shown to be annular in configuration, it will be appreciated that it may instead be of any desired shape.

The cover of the top member has been shown in its preferred form as being embossed in a floral design depicting a daisy. An artificial daisy of like shape may be contained within the recess so provided on the inside of the cover or otherwise removably situated within the container. Other designs on the cover are also contemplated or, alternatively, the cover may simply be planar.

Since certain changes may be made without departing from the scope of the invention herein contemplated, is intended that all matter shown in the drawings or described hereinabove be interpreted as being illustrative and not in a limited sense.

What is claimed is:

1. A holder for cleaning and storing dentures and having a denture contained therein, comprising,
    a disposable container for storing and cleaning a denture comprising superposed bottom and top members of the general configuration of a denture and which are adapted to receive for storage therebetween a full set of dentures, the bottom member having a base element and vertical wall means defining the periphery of the bottom member, the vertical wall means of the bottom member extending from the base element and being secured to the base element, the top member having a cover element and vertical wall means defining the periphery of the top member, the wall means of the top member extending from the cover element and being secured thereto, the superposed top and bottom members forming a closed chamber in which a denture can be stored and cleaned, the base element of the bottom member having a well disposed therein for retaining a water-soluble dentifrice in solid form;
    a denture seated on the base element of the bottom member over the well; and
    an aqueous medium filling the well and at least part of the rest of the bottom member to dissolve a dentifrice contained therein to form a dentifrice solution submerging the denture seated on the base element of the bottom member.

2. A holder as defined in claim 1 wherein the vertical wall means of the top member comprises a straight vertical wall element having opposed side edges and a curved vertical wall element extending from one of the side edges of the straight vertical wall element to the other side edge of the straight vertical wall element, the vertical wall elements being joined to each other and to the cover element of the top member.

3. A holder as defined in claim 2 wherein the cover is embossed in a floral design.

4. A holder as defined in claim 1 wherein the cover element is substantially planar.

5. A holder as defined in claim 1 wherein the bottom member is of slightly smaller dimensions than the top member.

6. A holder as defined in claim 1 wherein the top and bottom members are separable.

7. A holder as defined in claim 1 wherein the top and bottom members are hinged together as a unitary structure with the top member being pivotable to an open position for removing the denture and emptying the dentifrice solution contained in the holder.

8. A holder as defined in claim 7 wherein the top and bottom members are hinged together by a living hinge.

* * * * *